(12) United States Patent
Ouchi

(10) Patent No.: US 6,299,612 B1
(45) Date of Patent: Oct. 9, 2001

(54) WIRE LOOP TYPE INSTRUMENT FOR ENDOSCOPE AND METHOD OF PRODUCING THE SAME

(75) Inventor: Teruo Ouchi, Saitama (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/363,839

(22) Filed: Jul. 30, 1999

(30) Foreign Application Priority Data

Sep. 2, 1998 (JP) .................................................. 10-248033

(51) Int. Cl.⁷ .................................................. A61B 18/18
(52) U.S. Cl. .............................................. 606/47; 606/113
(58) Field of Search ................................ 606/41, 47, 113, 606/127, 128

(56) References Cited

U.S. PATENT DOCUMENTS

| 4,046,150 | * | 9/1977 | Schwartz et al. | 606/127 |
| 4,311,143 | * | 1/1982 | Komiya | 606/47 |
| 4,503,855 | * | 3/1985 | Maslanka | 606/47 |
| 4,633,871 | | 1/1987 | Shinozuka. | |
| 5,171,233 | * | 12/1992 | Amplatz et al. | 606/127 |
| 5,376,094 | * | 12/1994 | Kline | 606/113 |

FOREIGN PATENT DOCUMENTS

| 52-12792 | 10/1975 | (JP). |
| 63-65852 | 3/1988 | (JP). |
| 3-18815 | 2/1991 | (JP). |
| 5176941 | 7/1993 | (JP). |

* cited by examiner

*Primary Examiner*—Michael Peffley
(74) *Attorney, Agent, or Firm*—Greenblum & Bernstein P.L.C.

(57) ABSTRACT

A wire loop type instrument for an endoscope has a control wire axially movably inserted in a flexible sheath, and a wire loop connected to the distal end of the control wire. The wire loop is formed by an elastic wire. When the control wire is advanced, the wire loop projects from the distal end of the flexible sheath and expands in a loop shape by its own elasticity. When the control wire is retracted, the wire loop is pulled into the distal end of the flexible sheath and folded. The elastic wire is a stranded wire formed by twisting together a plurality of thin metal wires. The control wire is formed by twisting together a pair of elastic wires extending from the rear end of the wire loop in the opposite direction to the direction of twist of each elastic wire.

2 Claims, 6 Drawing Sheets

US 6,299,612 B1

WIRE LOOP TYPE INSTRUMENT FOR ENDOSCOPE AND METHOD OF PRODUCING THE SAME

BACKGROUND OF THE INVENTION

The present disclosure relates to subject matter contained in Japanese Patent Application No. 10248033 (filed on Sep. 2, 1998), which is expressly incorporated herein by reference in its entirety.

1. Field of the Invention

The present invention relates to a wire loop type instrument that is removably inserted into an instrument-inserting channel of an endoscope to carry out excision or the like. The present invention also relates to a method of producing the wire loop type instrument.

2. Description of the Prior Art

FIG. 7 shows a distal end portion of a conventional high-frequency snare for use with an endoscope. In a flexible sheath 1, a control wire 2 is axially movably inserted, and a wire loop 3 formed from an elastic wire is connected to the distal end of the control wire 2 through a connecting pipe 4.

Consequently, the wire loop 3 projects from or withdraws into the distal end of the flexible sheath 1 in response to an operation of advancing or retracting the control wire 2 in the axial direction. When projecting from the distal end of the flexible sheath 1, the wire loop 3 expands in a loop shape by its own elasticity. When pulled into the distal end of the flexible sheath 1, the wire loop 3 is folded.

In the conventional endoscopic high-frequency snare having the above-described structure, however, the inner diameter d of the flexible sheath 1 must be so large that the connecting pipe 4, which connects together the wire loop 3 and the control wire 2, can smoothly move back and forth in the flexible sheath 1.

Accordingly, the flexible sheath 1 becomes thick, and because of the large inner diameter of the flexible sheath 1, when the wire loop 3 is pulled into the flexible sheath 1 to excise a polyp, the polyp pinched tight with the wire loop 3 may be undesirably drawn into the flexible sheath 1, together with the wire loop 3. This may hinder the polyp excision treatment. There are also cases where the polyp cannot be removed from the wire loop 3. In addition, because the outer diameter of the flexible sheath 1 becomes large, the range of applications of the high-frequency snare is unfavorably limited. That is, it is usable only in endoscopes having an instrument-inserting channel with a sufficiently large diameter.

SUMMARY OF THE INVENTION

An object of the present invention is to provide a wire loop type instrument for an endoscope that allows a reduction in diameter of the flexible sheath, which will be directly associated with the improvement in function, and that is easy to manufacture and also easy to use. Another object of the present invention is to provide a method of producing the wire loop type instrument.

Other objects and advantages of the present invention will become apparent from the following detailed description of illustrated embodiments of the invention.

According to the present invention, there is provided a wire loop type instrument for an endoscope having a control wire axially movably inserted in a flexible sheath, and a wire loop connected to the distal end of the control wire. The wire loop is formed by an elastic wire. When the control wire is advanced axially, the wire loop projects from the distal end of the flexible sheath and expands in a loop shape by its own elasticity. When the control wire is retracted axially, the wire loop is pulled into the distal end of the flexible sheath and folded. The elastic wire that forms the wire loop is a stranded wire formed by twisting together a plurality of thin metal wires. The control wire is formed by twisting together a pair of elastic wires extending from the rear end of the wire loop in the opposite direction to the direction of twist of each of the elastic wires.

In addition, there is provided a method of producing a wire loop type instrument for an endoscope having a control wire axially movably inserted in a flexible sheath, and a wire loop connected to the distal end of the control wire. The wire loop is formed by an elastic wire. When the control wire is advanced axially, the wire loop projects from the distal end of the flexible sheath and expands in a loop shape by its own elasticity. When the control wire is retracted axially, the wire loop is pulled into the distal end of the flexible sheath and folded. The method includes the step of forming the wire loop with an elastic wire which is a stranded wire formed by twisting together a plurality of thin metal wires, and the step of twisting together a pair of elastic wires extending from the rear end of the wire loop in the opposite direction to the direction of twist of each of the elastic wires, thereby forming the control wire.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
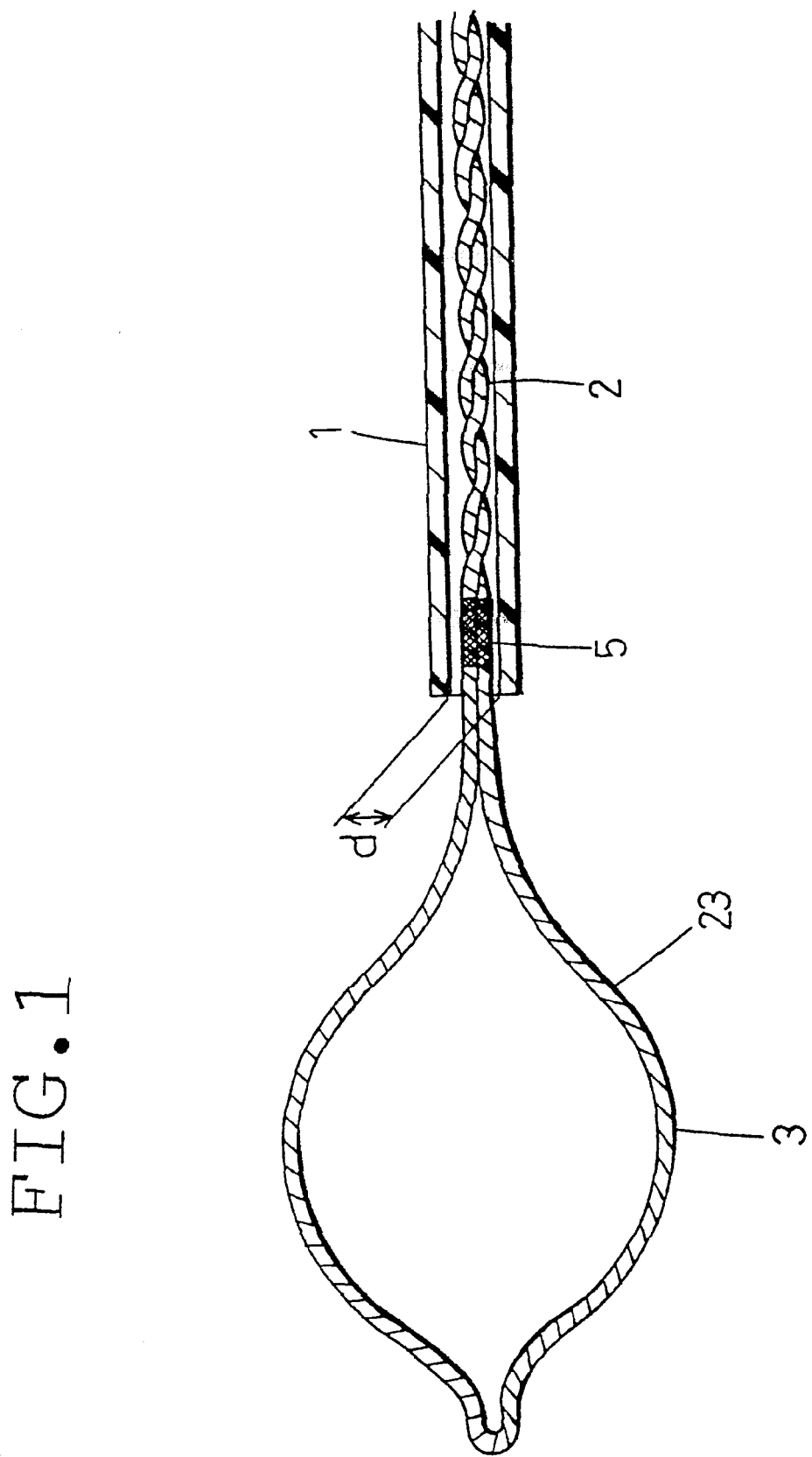
FIG. 1 is a sectional plan view of a distal end portion of a high-frequency snare for an endoscope according to a first embodiment of the present invention.

FIG. 1 shows a distal end portion of a wire loop type instrument for an endoscope according to a first embodiment of the present invention. A flexible sheath 1 is formed from a tetrafluoroethylene resin tube, for example. The flexible sheath 1 is removably inserted into an instrument-inserting channel of an endoscope (not shown).

A wire loop 3 is formed by a single electrically conductive elastic wire 23 bent back at an intermediate point thereof to define a loop shape. Under conditions where no external force is applied thereto, the wire loop 3 forms a smoothly curved loop with a diameter of several centimeters.

As the elastic wire 23, a stainless-steel stranded wire with a diameter of the order of from 0.2 mm to 0.5 mm is used by way of example. The elastic wire 23 is formed by twisting together a plurality (e.g. from three to seven) of thin stainless-steel wires.

The wire loop 3 can be folded by elastic deformation of the elastic wire 23 by application of external force. When the external force is removed, the wire loop 3 is returned to the original loop shape by the elasticity of the elastic wire 23.

A flexible control wire 2 is axially movably inserted in the flexible sheath 1. The control wire 2 is formed by twisting together a pair of portions of the elastic wire 23 that extend in side-by-side relation from the rear end of the wire loop 3 (the pair of portions of the elastic wire 23 will hereinafter be referred to as "two elastic wires 23"), thereby forming a single wire serving as the control wire 2.

It should be noted that the direction of twist of the two elastic wires 23, which form the control wire 2, is opposite to the direction of twist of each elastic wire 23. The two elastic wires 23 are secured to each other by silver-alloy brazing, plasma arc welding or the like at a boundary portion 5 between the wire loop 3 and the control wire 2. The details of this portion of the wire loop type instrument will be described later, together with the manufacturing method thereof.

Figure 2:
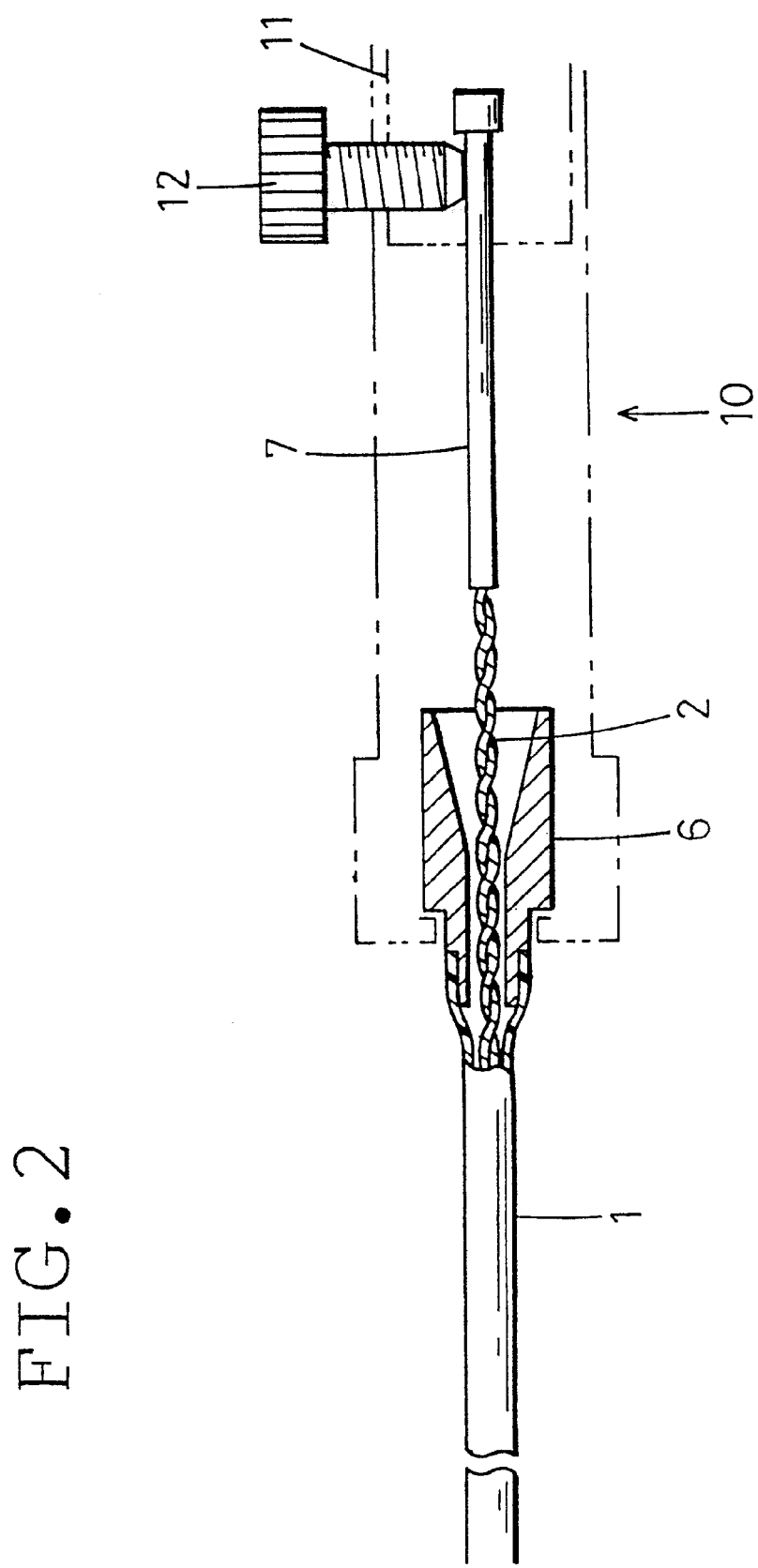
FIG. 2 is a sectional side view of a proximal end portion of the high-frequency snare according to the first embodiment of the present invention.

FIG. 2 shows a proximal end portion of the flexible sheath 1. A connecting member 6 is attached to the proximal end of the flexible sheath 1. The connecting member 6 is connected to a control part 10 of the wire loop type instrument. A proximal end portion of the control wire 2 that extends from the connecting member 6 is inserted into a metallic connecting pipe 7 and secured thereto integrally. The connecting pipe 7 is connected and secured to an operating member 11 in the control part 10 by a setscrew 12, for example.

Consequently, in response to an operation of advancing or retracting the operating member 11 at the control part 10, the control wire 2 moves axially in the flexible sheath 1. When the control wire 2 moves forward, the wire loop 3 projects from the distal end of the flexible sheath 1 to expand. When the control wire 2 moves backward, the wire loop 3 withdraws into the distal end of the flexible sheath 1 to contract.

The control part 10 is provided with a connecting terminal (not shown) for electrically connecting a high-frequency power supply cord (not shown) to the control wire 2. Thus, a high-frequency electric current can be supplied to the wire loop 3 through the control wire 2. The setscrew 12 can also be used as a connecting terminal.

Figure 3:
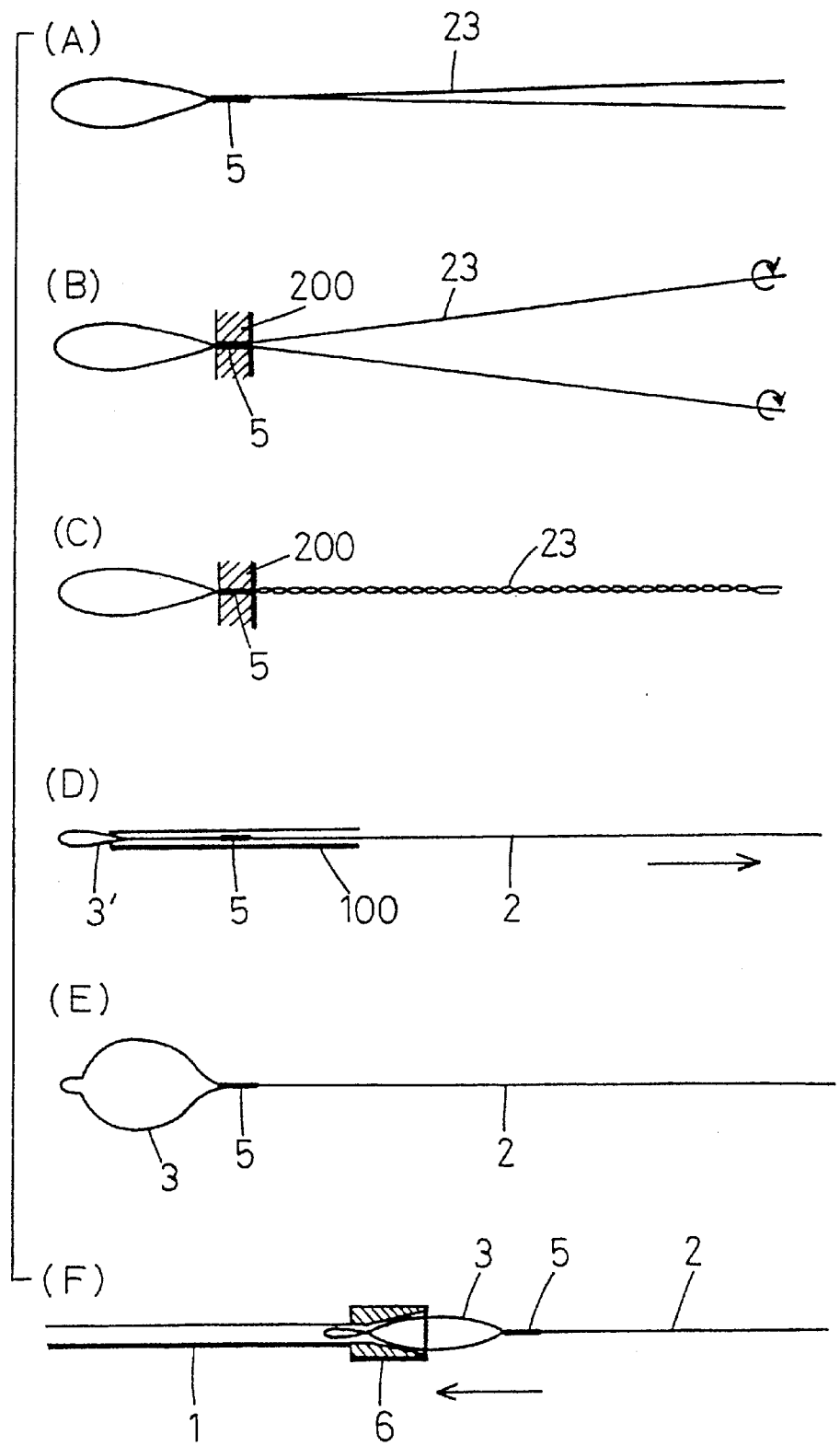
FIGS. 3A–3F are schematic views showing the steps in the process of manufacturing the high-frequency snare according to the first embodiment of the present invention.

FIG. 3 shows a sequence of steps of producing the wire loop 3 and the control wire 2. First, as shown in part (A) of FIG. 3, a single elastic wire 23 is gently bent back at an intermediate point thereof, and two halves of the bent elastic wire 23 are laid on one another in parallel at the boundary portion 5 between the wire loop 3 and the control wire 2 and secured to each other at the boundary portion 5 by silver-alloy brazing or plasma arc welding, for example.

It should be noted that the secured portion 5 is shown to be somewhat thick in FIG. 3 so as to be easily identified. In actuality, the two halves of the elastic wire 23 are fixed to each other at the portion 5 so that the outer diameter of the portion 5 will not be larger than the sum total of the diameters of the two halves of the elastic wire 23.

Next, as shown in part (B) of FIG. 3, the boundary portion 5 is firmly fixed with a vice 200 or the like, and in this state, two elastic wires 23 extending rearward from the boundary portion 5 are twisted about their respective axes by the same number of twists in a direction in which each stranded elastic wire 23 is further twisted.

Regarding the twisting direction of stranded wires, there are right-hand twist and left-hand twist (generally known as "S-twist" and "Z-twist", respectively). If it has been given S-twist (right-hand twist), each elastic wire 23 is further given right-hand twist at the step (B).

The number of twists given to each elastic wire 23 at the step (B) is about 50 twists with respect to a length of 2 m, for example. Thus, the twist in each elastic wire 23 is increased within the elastic deformation region. If the twisting force applied to each elastic wire 23 is removed, the elastic wire 23 untwists and returns to the previous state.

Next, as shown in part (C) of FIG. 3, the two elastic wires 23 extending rearward from the boundary portion 5 are twisted together in the opposite direction to the direction of twist of each elastic wire 23, thereby forming a single wire serving as the control wire 2.

At this time, it is unnecessary to apply force to each elastic wire 23. The two elastic wires 23 are laid parallel and adjacent to each other with the twisting force kept applied thereto so that each elastic wire 23 will not untwist. Thereafter, the twisting force is removed. Consequently, the two elastic wires 23 are twisted together in the opposite direction to the direction of twist of each elastic wire 23 by the untwisting action of each elastic wire 23 and stabilize in a natural state in the form of a single wire.

By doing so, the rotation of each of the two elastic wires 23 and the twisting rotation of the two elastic wires 23 are allowed to cancel each other. Accordingly, the two elastic wires 23 can be twisted together easily without disordering the twisted condition. In addition, the wire loop 3 will not rotate when the control wire 2 is pushed or pulled.

Upon completion of the control wire 2 by the above-described process, as shown in part (D) of FIG. 3, the elastic wire 23 is passed through a jig 100 from the control wire (2) side thereof. The jig 100 is a metallic pipe having an appropriate diameter and length. As a result, a portion 3' to be formed into a wire loop is bent into a U-shape of perfect symmetry at the distal end thereof.

Finally, as shown in part (E) of FIG. 3, the wire loop 3 is formed into a predetermined shape. As a result, the wire loop 3 and the control wire 2 are completed. Then, as shown in part (F) of FIG. 3, the elastic wire 23 is inserted into the connecting member 6, which is attached to the proximal end of the flexible sheath 1, from the wire loop (3) side. Consequently, the wire loop 3 folds and passes through the flexible sheath 1 in the folded state. Thus, the wire loop type instrument is completed as shown in FIG. 1.

In the wire loop type instrument for an endoscope arranged as stated above, it is appropriate that the inner diameter d of the flexible sheath 1 should be larger than the diameter of the control wire 2 by about 0.1 to 0.5 mm with a view to allowing the control wire 2, which is formed from the two twisted elastic wires 23, to move back and forth smoothly in the flexible sheath 1.

Accordingly, assuming that the diameter of the elastic wire 23 is 0.5 mm, if the inner diameter d of the flexible sheath 1 is set larger than the diameter of the control wire 2 by 0.2 mm, the inner diameter d is 1.2 mm. consequently, assuming that the wall thickness of the flexible sheath 1 is 0.3 mm, the outer diameter of the flexible sheath 1 is 1.8 mm. Thus, the wire loop type instrument can be used in an endoscope having an instrument-inserting channel with an inner diameter of 2 mm.

Moreover, because the inner diameter d of the flexible sheath 1 can be minimized, a polyp will not be drawn into the flexible sheath 1 when the control wire 2 is pulled to bind the polyp tight with the wire loop 3. Accordingly, the polyp excision treatment can be carried out safely and speedily.

Figure 4:
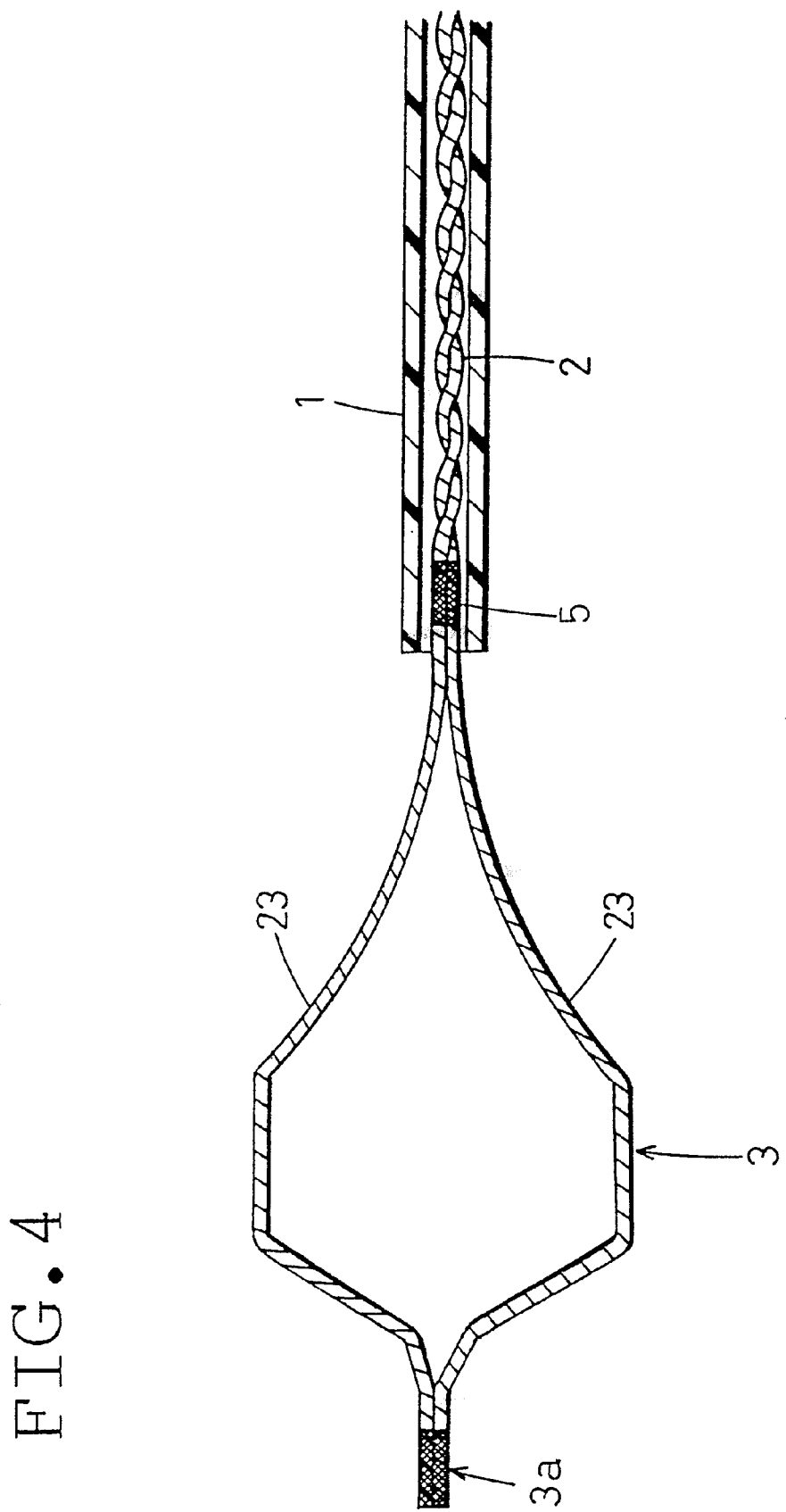
FIG. 4 is a sectional plan view of a distal end portion of a high-frequency snare for an endoscope according to a second embodiment of the present invention.

FIG. 4 shows a high-frequency snare for an endoscope according to a second embodiment of the present invention. In this embodiment, two elastic wires 23 are used as stock wires for producing the high-frequency snare. The two elastic wires 23 are secured to each other at distal end portions 3a thereof by silver-alloy brazing, plasma arc welding or the like to form a wire loop 3. The arrangement of the rest of this embodiment is the same as that of the above-described first embodiment.

Figure 5:
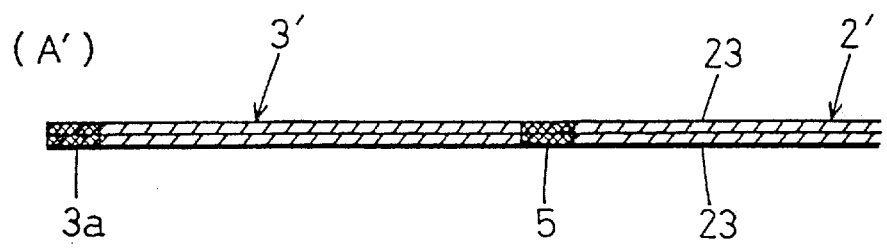
FIG. 5 is a schematic view showing the first step in the process of manufacturing the high-frequency snare according to the second embodiment of the present invention.

To produce a wire loop 3 and control wire 2 in this embodiment, as shown at (A') in FIG. 5, two elastic wires 23 superimposed on one another are secured to each other at a boundary portion 5 between a portion 3' to be formed into a wire loop and a portion 2' to be formed into a control wire and also at a distal end portion 3a.

Thereafter, the two elastic wires 23 are twisted together in the opposite direction to the direction of twist of each elastic wire 23 as in the case of the first embodiment [see parts (B) and (C) of FIG. 3]. Thus, the wire loop 3 and the control wire 2 are formed.

Figure 6:
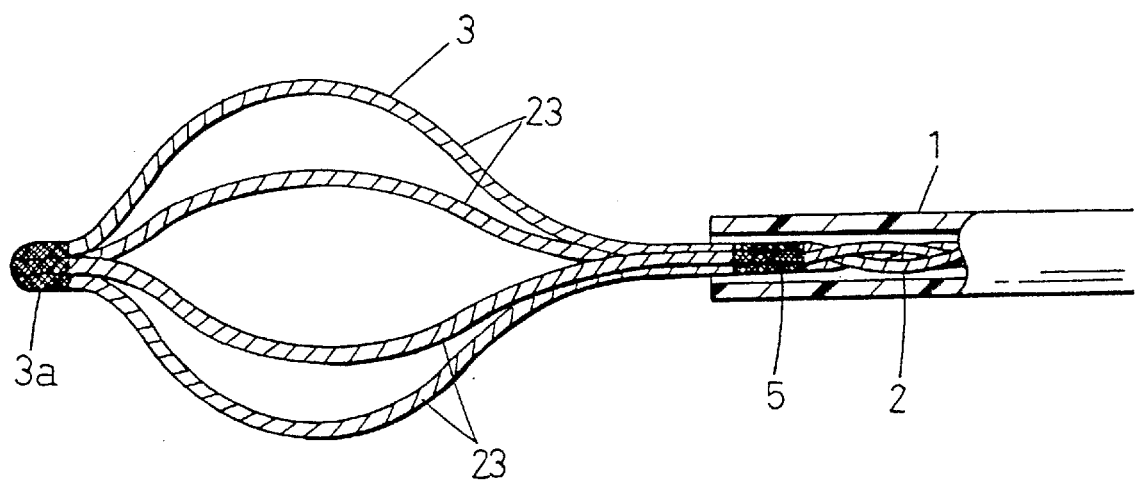
FIG. 6 is a sectional plan view of a distal end portion of a basket type foreign body-recovering instrument for an endoscope according to a third embodiment of the present invention.
Figure 7:
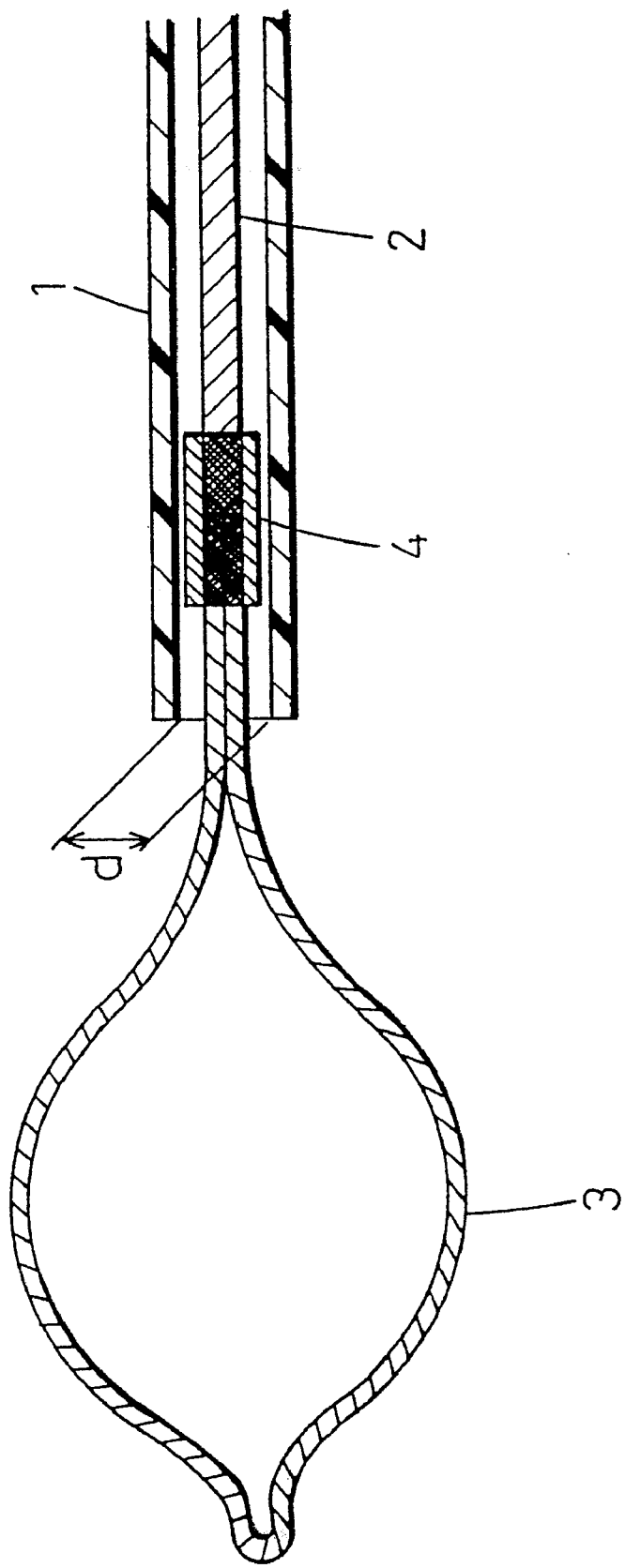
FIG. 7 is a sectional plan view of a distal end portion of a conventional high-frequency snare for an endoscope.

FIG. 6 shows an embodiment in which the present invention is applied to a basket type foreign body-recovering instrument for an endoscope. In this embodiment, the wire loop 3 is formed from a plurality of pairs of elastic wires 23 (e.g. four elastic wires), and a control wire 2 is formed by twisting together all the elastic wires 23 in the opposite direction to the direction of twist of each elastic wire 23.

To produce the basket type foreign body-recovering instrument, first, all the elastic wires 23 are secured together at a boundary portion 5 between a portion to be formed into a wire loop 3 and a portion to be formed into a control wire 2 and also at a distal end portion 3a as in the case of the above-described embodiment.

The four elastic wires 23 may be twisted together in such a manner that after each pair of elastic wires 23 have been twisted together, the two pairs of elastic wires 23 are twisted together.

According to the present invention, a stranded wire formed by twisting together a plurality of thin metal wires is used as an elastic wire for forming a wire loop, and a pair of elastic wires extending from the rear end of the wire loop are twisted together to form a control wire. Therefore, the diameter of a boundary portion between the wire loop and the control wire can be prevented from becoming larger than the diameter of the control wire. Accordingly, the flexible sheath can be formed with a reduced outer diameter.

Consequently, the wire loop type instrument according to the present invention can be used in an endoscope having an instrument-inserting channel with a small diameter. When the wire loop type instrument is used to excise a polyp, the polyp will not be drawn into the flexible sheath. Accordingly, the polyp excision treatment can be carried out safely and speedily.

In addition, because the direction in which the elastic wires are twisted together is opposite to the direction of twist of each elastic wire, the rotation of each of the two elastic wires and the twisting rotation of the two elastic wires are allowed to cancel each other. Therefore, the two elastic wires can be twisted together easily without disordering the twisted condition. In addition, the wire loop will not rotate when the control wire is pushed or pulled. Thus, the wire loop type instrument is easy to use.

While the invention has been described by reference to specific embodiments chosen for purposes of illustration, it should be apparent that numerous modifications could be made thereto by those skilled in the art without departing from the basic concept and scope of the invention.

What is claimed is:

1. A method of producing a wire loop type instrument for an endoscope having a control wire axially movably inserted in a flexible sheath, and a wire loop connected to a distal end of said control wire, said wire loop being formed by an elastic wire, wherein when said control wire is advanced axially, said wire loop projects from a distal end of said flexible sheath and expands in a loop shape by its own elasticity, whereas when said control wire is retracted axially, said wire loop is pulled into the distal end of said flexible sheath and folded, said method comprising:

forming said wire loop with an elastic wire which is a stranded wire formed by twisting together a plurality of thin metal wires; and twisting together a pair of said elastic wires extending from a rear end of said wire loop in an opposite direction to a direction of twist of each of said elastic wires, thereby forming said control wire.

2. A method of producing a wire loop type instrument according to claim 1, wherein said pair of elastic wires are secured to each other so that an outer diameter of a mutually secured portion of said pair of elastic wires at said boundary portion is not larger than a sum total of diameters of said pair of elastic wires.

* * * * *